United States Patent

Tuunanen

[11] Patent Number: 6,020,211
[45] Date of Patent: *Feb. 1, 2000

[54] SEPARATION OF MAGNETIC MICROPARTICLES INVOLVING A PRECONCENTRATION STEP

[75] Inventor: Jukka Tuunanen, Helsinki, Finland

[73] Assignee: Labsystems OY, Finland

[*] Notice: This patent issued on a continued prosecution application filed under 37 CFR 1.53(d), and is subject to the twenty year patent term provisions of 35 U.S.C. 154(a)(2).

[21] Appl. No.: 08/817,691

[22] PCT Filed: Oct. 20, 1995

[86] PCT No.: PCT/FI95/00579

§ 371 Date: Jun. 3, 1997

§ 102(e) Date: Jun. 3, 1997

[87] PCT Pub. No.: WO96/12960

PCT Pub. Date: May 2, 1996

[30] Foreign Application Priority Data

Oct. 20, 1994 [FI] Finland ................. 944939

[51] Int. Cl.$^7$ ............................ G01N 33/553
[52] U.S. Cl. .................. 436/526; 210/222; 210/695; 294/65.5; 335/295; 422/50; 422/68.1; 435/283.1; 435/287.1; 435/287.2; 436/177; 436/806
[58] Field of Search ................. 210/222, 695; 294/65.5; 335/295; 422/50, 68.1, 100, 101; 435/283.1, 287.1, 287.2; 436/526, 177, 806

[56] References Cited

U.S. PATENT DOCUMENTS

| | | |
|---|---|---|
| 2,471,764 | 5/1949 | Miller et al. |
| 3,904,482 | 9/1975 | Mehl .................. 195/109 |
| 3,970,518 | 7/1976 | Giaever ............... 195/1.5 |
| 3,985,649 | 10/1976 | Eddelman . |
| 4,018,886 | 4/1977 | Giaever ............... 424/12 |
| 4,115,535 | 9/1978 | Giaever ............... 424/1 |

(List continued on next page.)

FOREIGN PATENT DOCUMENTS

| | | |
|---|---|---|
| 0027008 A1 | 4/1981 | European Pat. Off. . |
| 0186001 | 7/1986 | European Pat. Off. . |
| 0042755 B1 | 8/1988 | European Pat. Off. . |
| 0 317 286 | 5/1989 | European Pat. Off. . |
| 0 351 857 | 1/1990 | European Pat. Off. . |
| 0 358 948 | 3/1990 | European Pat. Off. . |
| 0 479 448 A3 | 4/1992 | European Pat. Off. . |
| 0522322 | 1/1993 | European Pat. Off. . |
| 2824742 A1 | 2/1979 | Germany . |
| 58-5656 | 1/1983 | Japan . |
| 58-5657 | 1/1983 | Japan . |
| 58-5658 | 1/1983 | Japan . |
| 63-5263 | 1/1988 | Japan . |
| 63-5265 | 1/1988 | Japan . |
| 63-5266 | 1/1988 | Japan . |
| 1414479 | 11/1975 | United Kingdom . |
| 2147 698 | 5/1985 | United Kingdom . |
| 2147898 | 5/1985 | United Kingdom . |
| WO 86/06493 | 11/1986 | WIPO . |
| WO 87/05536 | 9/1987 | WIPO . |
| WO 94/18565 | 8/1994 | WIPO . |
| WO 9418564 | 8/1994 | WIPO . |
| WO 9500247 | 1/1995 | WIPO . |
| WO 9612958 | 5/1996 | WIPO . |
| WO 9612959 | 5/1996 | WIPO . |
| WO 9612960 | 5/1996 | WIPO . |
| WO 9612961 | 5/1996 | WIPO . |

*Primary Examiner*—Christopher L. Chin
*Assistant Examiner*—Pensee T. Do
*Attorney, Agent, or Firm*—Fish & Richardson P.C.

[57] ABSTRACT

The invention relates to a method for separating magnetic particles from a composition in a vessel. In the method, particles are first concentrated on the wall of the vessel and collected from this area by using a separation means (1) to which the magnetic particles adhere. In this way, particles can be collected efficiently. The invention can be used in different applications especially in the fields of biotechnology, biochemistry, and biomedicine.

17 Claims, 6 Drawing Sheets

U.S. PATENT DOCUMENTS

| | | | |
|---|---|---|---|
| 4,200,613 | 4/1980 | Alfrey et al. | 422/71 |
| 4,272,510 | 6/1981 | Smith et al. | 427/47 |
| 4,438,068 | 3/1984 | Forrest | 422/61 |
| 4,495,151 | 1/1985 | Ohyama et al. | 422/102 |
| 4,649,116 | 3/1987 | Daty et al. | 435/287 |
| 4,731,337 | 3/1988 | Luotola et al. | 436/526 |
| 4,751,053 | 6/1988 | Dodin et al. . | |
| 4,891,321 | 1/1990 | Hubscher | 435/293 |
| 4,895,650 | 1/1990 | Wang . | |
| 5,167,926 | 12/1992 | Kimura et al. | 422/67 |
| 5,200,084 | 4/1993 | Liberti et al. | 210/295 |
| 5,206,034 | 4/1993 | Yamazaki | 425/145 |
| 5,318,914 | 6/1994 | Matte et al. . | |
| 5,466,574 | 11/1995 | Liberti et al. | 435/5 |
| 5,474,742 | 12/1995 | Tuuminen | 422/63 |
| 5,647,994 | 7/1997 | Tuunanen et al. | 210/695 |

SEPARATION OF MAGNETIC MICROPARTICLES INVOLVING A PRECONCENTRATION STEP

This Application is a 371 of PCT/FI95/00579, filed Oct. 20, 1995, which claims Priority to Findland 944939 filed Oct. 20, 1994.

BACKGROUND OF THE INVENTION

1. Technical Field

The invention relates to the separation of magnetic particles from a composition. The invention can be used in different applications, especially in the fields of biotechnology, biochemistry, and biomedicine.

2. Technical Background

Magnetic particles are used as a solid phase in various applications to bind biomaterial. One advantage of microparticles is the large area of the solid phase and short diffusion lengths. The size of microparticles is generally 0.05–10 $\mu$M and they are available in different materials and already activated for many applications. Magnetic particles can be moved by using a magnetic field.

The separation methods of magnetic particles currently used include settling a reaction vessel in a magnetic field so that particles are accumulated into a so-called pellet at the bottom of vessel. Thereafter, the liquid which is free from particles is decanted or removed by aspiration. However, the removing of the liquid from the vessel must be carried out very carefully so as not to remove the particles at the same time.

Publication EP-140787 (corresponding to publication U.S. PAT. No. 4,649,116) proposes a method by which micro-size magnetic particles are separated from a liquid by using a magnetic rod which is pushed thereto. The particles are pulled off the rod by using a stronger magnet.

Publication WO-86/06493 suggests a method to be used in immunoassays, in which magnetic particles and the marked complex adhered to them are separated from a liquid by using a magnetic rod and subsequently taken to be measured. The tip of the rod comprises a fixed magnet and a removable protective cover to whose outer surface the particles adhere. It is preferable to cover the protective cover with another cover after the separation and before measuring. After the measurement, the protective covers are detached, together with the particles, and thrown away and new covers are taken for a new separation. According to the publication, the magnet can also be an electromagnet, whereby the magnetic field can be eliminated when desired.

Publication WO-87/05536 suggests a device for separating magnetic particles, comprising, on the inside, a rod movable in a vertical boring and a magnet at the lower end thereof. The device is introduced, with the magnet in the lower position, into a liquid containing particles, whereby the particles are accumulated on the end of the rod. When the magnet is allowed into the upper position, the particles can be detached from the rod. In this way, particles can be collected and transferred from one liquid to another.

However, the disclosed separation methods of magnetic particles cannot be applied very well in-objects of use in which particles must be collected from a fairly large volume compared with the separation device.

SUMMARY OF THE INVENTION

Now, a separation method according to claim 1 has been invented. The other claims describe some preferred embodiments of the invention.

According to the invention, particles are separated from a composition so that the particles are first concentrated on one spot in the vessel from where they are then collected by using a magnetic separation means. In this way, particles can be collected effectively.

The concentration can be effected by using a magnetic field or gravitation, or by centrifuging. In most cases, it is preferable to use a magnet.

The collecting of particles is preferably carried out by using an elongated separation means comprising a magnetic field that effects at the lower end thereof. It is preferable to use a longitudinal magnetic field whose strength and gradient are at their maximum at the end of the separation means. The particles are thus accumulated in a concentrated manner at the end of the rod from where they can be detached into a small volume. It is also easy to collect the particles in a concentrated manner by using such a separation means.

The magnetic field is preferably positioned at the end of the separation means by using a long rod magnet. The proportion of the length of the rod magnet to its thickness is, e.g., at least about 2:1, preferably at least about 3:1, and most preferably at least about 12:1. The magnet is preferably sufficiently long so that the upper end of its dipole is above the compound when particles are being collected.

The rod magnet is preferably formed of a permanent magnet with a ferromagnetic arm as its extension. In this way, the magnet and the magnetised arm together function as a long rod magnet. The arm dissolves the gradient of the upper pole of the field, whereby the upper pole does not carry out the collection of particles. By using the ferromagnetic arm, the long rod magnet can be provided at relatively low cost. However, even with the ferromagnetic arm, it is advantageous to use a relatively long magnet (with the length of, e.g., about 2 . . . 10 times the diameter). The length of the magnet is preferably selected so that a maximum internal, permanent field intensity is provided for the magnet in question. The junction between the magnet and the arm is preferably made so that the arm and the magnet come inside one another for a short distance. In this way, the formation of strong gradients at the junction, which may possibly collect particles, is avoided.

The cross-section of the rod magnet can be, e.g., circular or rectangular. The circular shape is the best with respect to both manufacture and use. Indeed, the rotation of the magnet on its axis, for example, has no effect in this case. In principle, the rod can be curved to make the moving mechanisms simpler.

Particles can be detached from the separation means, when required, by any suitable manner, even mechanically or by using another magnet. However, particles are preferably detached by eliminating the effect of the magnetic field in the separation means. The separation means preferably comprises a protective cover and a rod with a magnet that is movable with respect to the cover.

The tip of the protective cover is preferably provided with a sharp, downward oriented projection. This minimises the amount of liquid remaining at the tip. The tip is typically cone-shaped. When transferring particles into very small vessels, the tip is preferably the shape of a concave cone.

The shape of the protective cover of the rod can vary according to the use. Normally, the circular shape is the most advantageous with respect to both manufacture and use. In order to increase strength, the cover can be made conical, which also facilitates the manufacture of the cover by injection moulding.

The method can be applied in both simple manual tools and automatic multichannel systems.

The invention is best adapted to be used for particles of about 1–10 μm.

BRIEF DESCRIPTION OF THE DRAWINGS

Some preferred applications of the invention are described in the following as examples. In the drawings of the description.

DETAILED DESCRIPTION OF THE INVENTION

Figure 1:
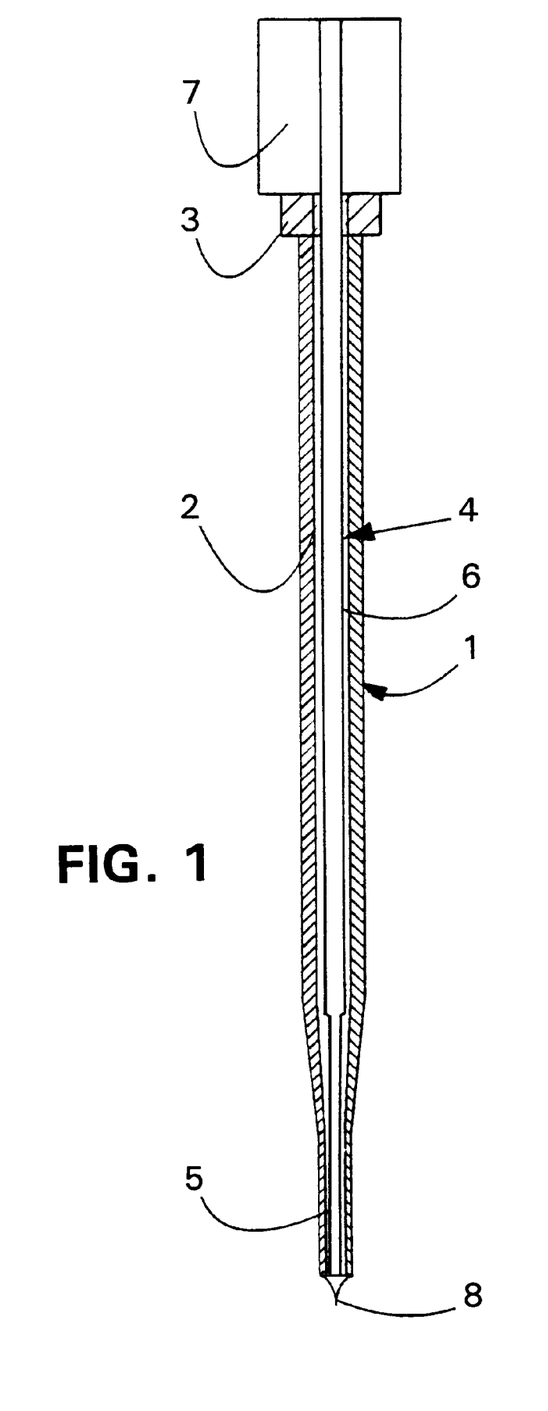
FIG. 1 presents a separation means useful for the invention.

The separation rod according to FIG. 1 comprises elongated protective cover 1 and a bore 2 in it. The lower ends of the protective cover and the boring are slightly tapered. The upper end of the body is provided with gripping knob 3.

Bore 2 comprises loose magnetic rod 4. This comprises vertical rod magnet 5 at the lower end thereof, and ferromagnetic arm 6 above it as an extension of the magnet. The end of the arm is provided with gripping knob 7.

The lower end of the cover is provided with a tapering, sharp-ended tip 8 with a concave surface. The length of the tip corresponds approximately to the width of the lower end of the cover.

The proportion of the length of magnet 5 to the diameter is about 10:1 and the proportion of the arm length to the length of the magnet is about 5:1. The arm is slightly thicker than the magnet and the upper end of the magnet is embedded inside the lower end of the arm at a length of about twice its diameter.

Tip 8 is especially well-adapted for transferring particles into a very small vessel, such as the well of a so-called HLA plate. In this case the tip is slightly longer than the height of the well and the diameter of the upper part of the tip is slightly smaller than the width of the well. When the tip is pushed into the well, the surface of the liquid rises along the surface of the tip due to surface tension. The edge of the moving surface of liquid sweeps the particles off the tip into the liquid. The detachment can be enhanced by stirring the rod. Correspondingly, when the tip is lifted from the well, the surface of the liquid moves towards the sharp end of the tip as an integral film. In this way, the liquid and the particles along it are completely detached from the tip.

Figure 2:
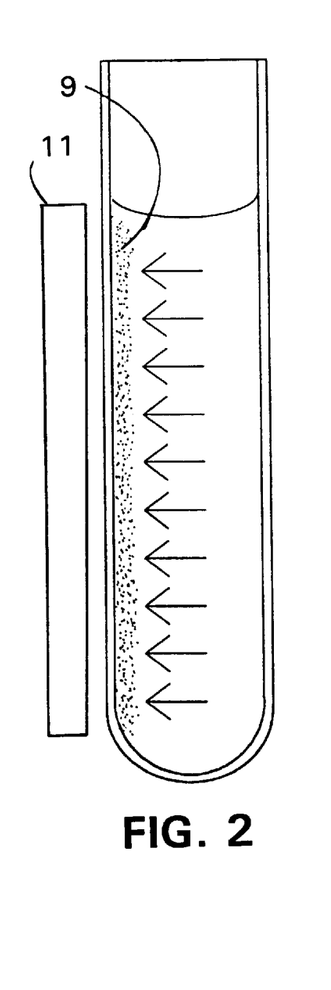
FIG. 2 presents the concentration of particles onto the wall of a test tube.
Figure 3:
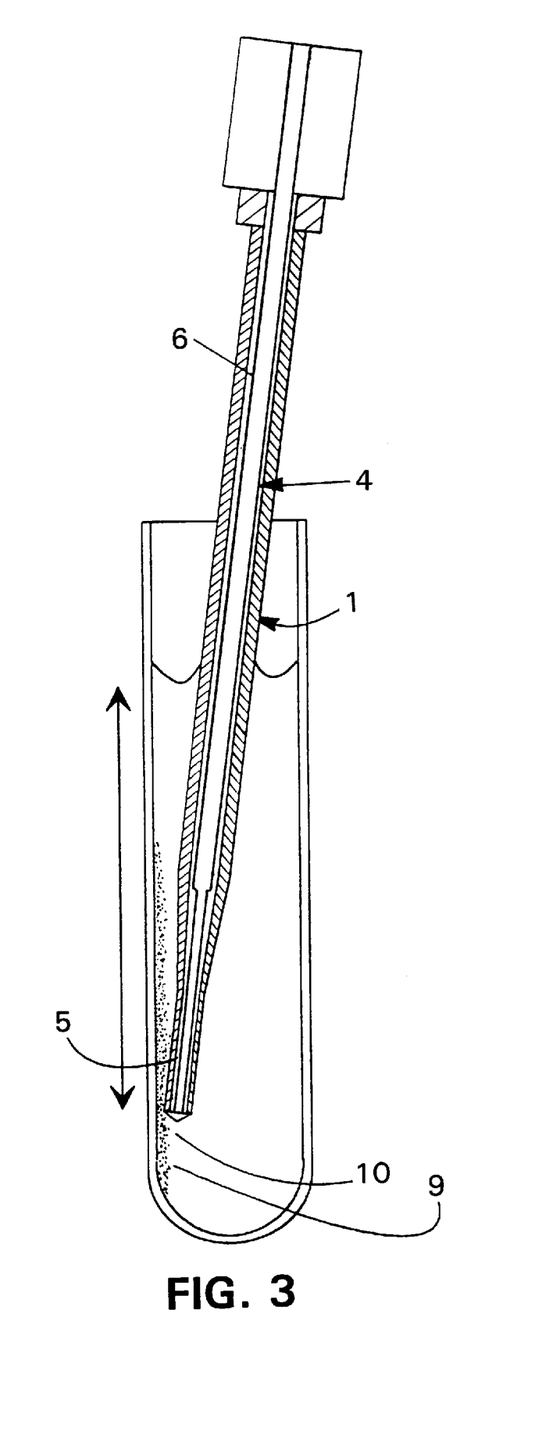
FIG. 3 presents the collection of particles from the wall of the test tube.

FIGS. 2 and 3 show how the particles are first pulled onto the wall of a test tube, by using a magnet, to form vertical strip 9 from where they are collected by sweeping with the separation rod to form spot-like mass 10 at the tip of the rod. The width of magnet 11 is as large as the height of the column of liquid in the tube, the magnet being magnetised in the direction of its shorter side. Here the tip of protective cover 1 is shaped like a relatively blunt cone. This is well-adapted for transferring particles into vessels where the tip can be pushed properly into the liquid. In other respects, the separation rod is similar to that of FIG. 1.

The method according to FIGS. 2 and 3 was tested in transferring particles from a so-called Vacutainer tube (7 ml) into the well of a microtitration plate (50 μl). The concentration was carried out by using an NdFeB magnet of 7×5×70 mm. The separation rod comprised an NdFeB magnet (d 3 mm, l 2 mm). On the basis of preliminary tests, the time spent for searching was about one minute.

According to one application, a test tube is used having a vertical, e.g., V-shaped groove, formed on the wall thereof. Particles settle in the groove to form as narrow a strip as possible, and it is also easy to move the separation means along the bottom of the groove to collect the particles.

Figure 4:
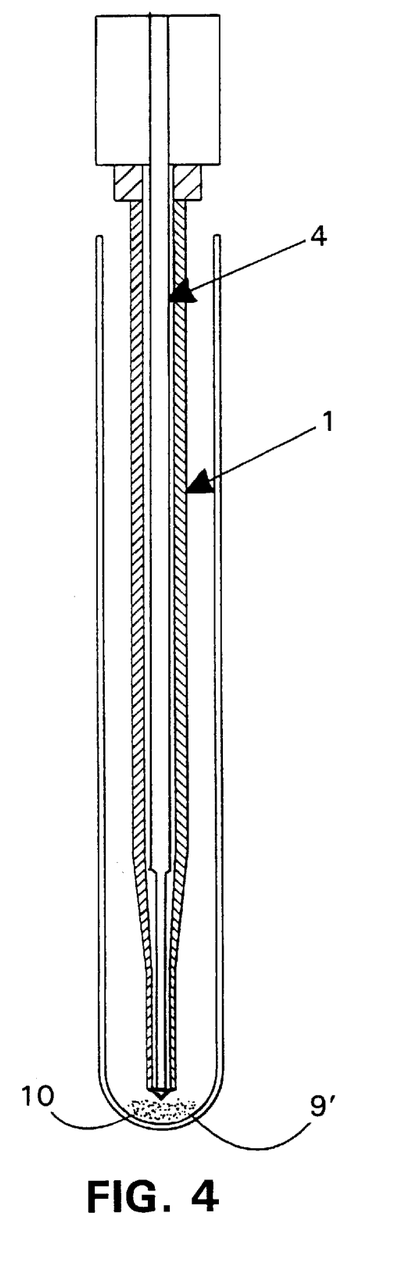
FIG. 4 presents the collection of particles from the bottom of the test tube.

FIG. 4 presents the collection of particles from the bottom of the test tube where they were first concentrated to form precipitate 9'. The precipitate is preferably provided by using gravitation or centrifuging. The separation rod is similar to that in FIG. 3.

Figure 5:
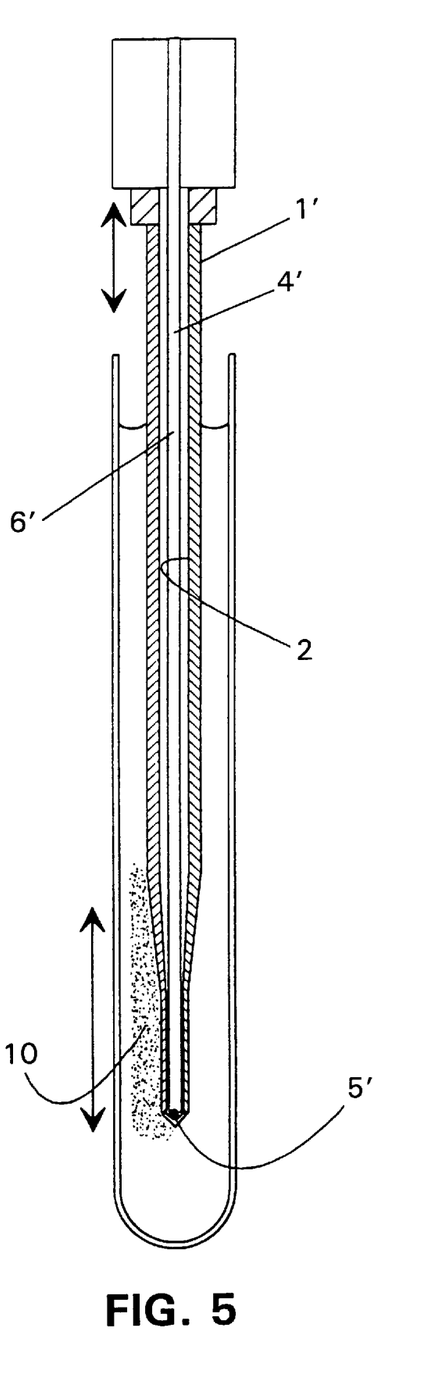
FIG. 5 presents the collection of particles from the wall of the test tube in another way.

FIG. 5 presents the collection of particles from the wall of the test tube by using another kind of separation rod. This also comprises movable rod 4' in bore 2 of protective cover 1'. Its tip is provided with a small magnet 5' and arm 6' is non-magnetic. The magnet is placed transversally with respect to the length of the rod. Here the particles are accumulated at the tip perpendicularly from the side to form mass 10'.

Figure 6:
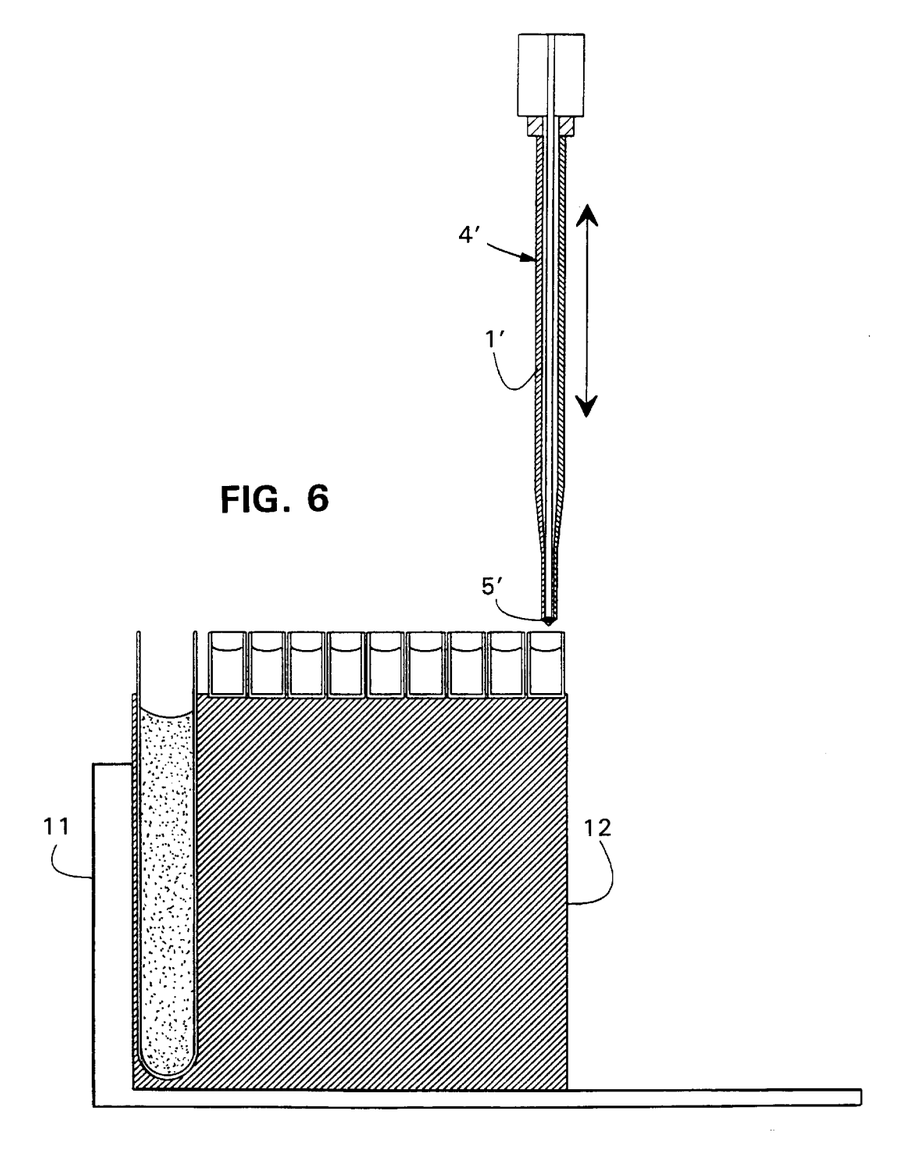
FIG. 6 presents a separation and transfer device useful for the invention in the stage of concentrating the particles.
Figure 7:
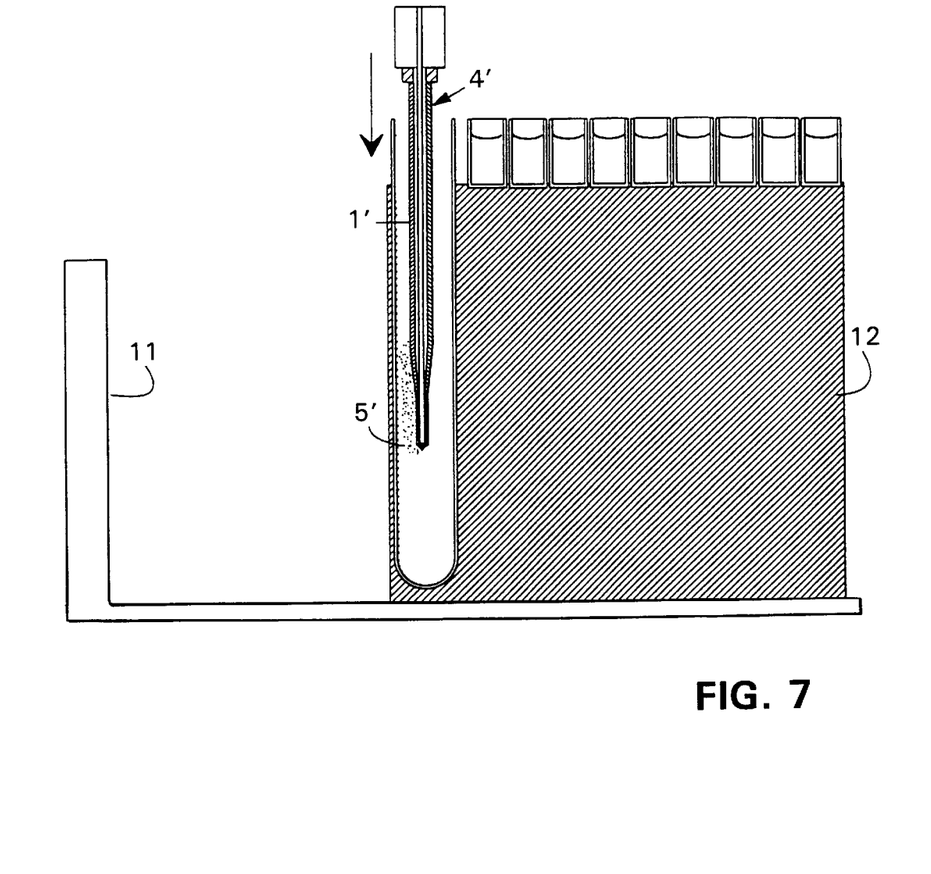
FIG. 7 presents the device of FIG. 6 in the stage of collecting the particles.

FIGS. 6 and 7 present a multichannel automatic device for implementing the method. The device employs separation rods according to FIG. 5. Particles are collected on the wall of the test tube by using rod magnets 11 situated in the body of the device on the side thereof. The test tubes from which the particles are collected are placed at the edge of carriage 12. The carriage can be moved with respect to the body so that the test tubes can be taken next to the magnets, whereby particles are concentrated on the walls of the tubes. Thereafter, the carriage is driven away from the magnets and particles are collected from the wall by using a separation rod movable with respect to the carriage. The carriage further comprises a microtitration plate on which the particles are transferred. The tips of the separation rods together with particles attached to them are taken to the desired well and the magnetic rods are lifted up, whereby the particles are released into the wells.

Figure 8:
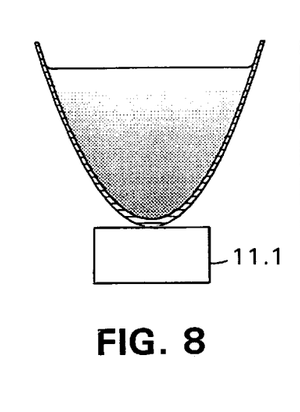
FIG. 8 presents the separation of particles onto the bottom of an elongated trough.
Figure 9:
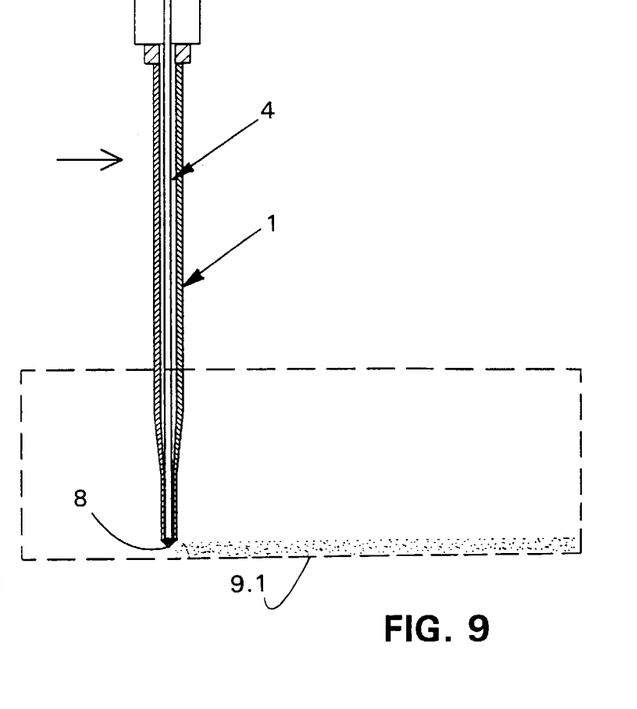
FIG. 9 presents the collection of particles from the trough of FIG. 8.

FIGS. 8 and 9 present the separation of particles from an elongated trough whose cross-section is tapered towards the bottom. Particles are pulled on the bottom of the trough to form a long horizontal line 9.1 by using magnet 11.1, thereafter, the magnet is moved further away and particles are collected by using the separation means. In this way, particles can be separated into their natural direction of settling over a relatively low layer of liquid. The separation is quick, the line remains well in its place and the collection is easy. The bottom of the trough is preferably provided with a V-groove, whereby particles are accumulated into as narrow a line as possible, making the collection as easy as possible.

Figure 10:
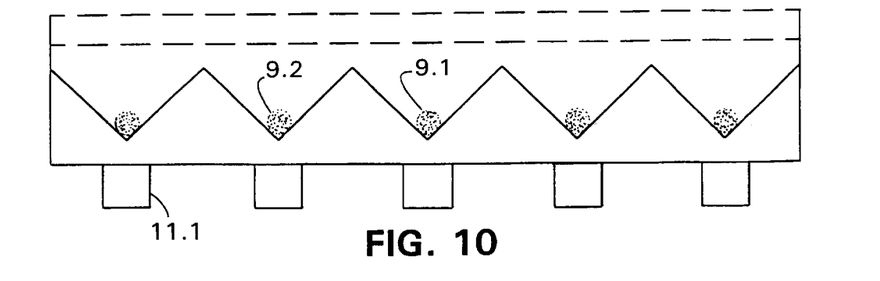
FIG. 10 presents the separation vessel comprising, on the bottom thereof, several grooves for separating the particles.

The application of FIG. 10 comprises a separation vessel that is provided with a number of parallel grooves with V-bottoms and, correspondingly, a number of magnets 11.1 are placed below the vessel. Particles are accumulated as narrow lines 9.2 at the bottom of the grooves. The surface of liquid is above the grooves, whereby the vessel can be filled in one operation. Alternatively, the grooves can be combined by transversal channels so that the surface of the liquid is at the same level in each groove.

I claim:

1. A method for separating magnetic particles from a composition in a vessel, comprising the steps of:
   (a) concentrating the particles on a wall of the vessel by using a magnetic field;
   (b) collecting the particles from the wall by using a magnetic probe to which the particles adhere; and
   (c) thereafter detaching the particles from the magnetic probe by eliminating the effect of the magnetic field of the magnetic probe.

2. A method according to claim 1, wherein the particles are concentrated on a side wall of the vessel to form a vertical strip.

3. A method according to claim 1, wherein the particles are concentrated to form a horizontal strip at the bottom of the vessel.

4. A method according to claim 1, wherein the wall contains a groove and the particles are concentrated to form a strip at the bottom of the groove.

5. A method for separating magnetic particles from a composition in a vessel, comprising the steps of:
   (a) concentrating the particles on a wall of the vessel by centrifugation, said particles ranging in diameter from about 0.05 µm to about 10 µm;
   (b) collecting the particles from the wall by using a magnetic probe to which the particles adhere; and
   (c) thereafter detaching the particles from the probe by eliminating the effect of the magnetic field of the magnetic probe.

6. A method for separating magnetic particles from a composition in a vessel, comprising the steps of:
   (a) concentrating the particles on a wall of the vessel, wherein the wall contains a groove and the particles are concentrated in a strip at the bottom of the groove;
   (b) collecting the particles from the wall by using a magnetic probe to which the particles adhere; and
   (c) thereafter detaching the particles from the magnetic probe by eliminating the effect of the magnetic field of the magnetic probe.

7. A device for separating magnetic particles from a composition, comprising:
   (a) a vessel for the composition containing the particles;
   (b) a magnet for concentrating the particles on a wall of the vessel; and
   (c) a magnetic probe for collecting the particles from the wall, wherein the magnetic probe comprises a separation rod within a protective cover that is movable with respect to the separation rod for release of the particles from the probe.

8. A device according to claim 7, wherein the separation rod comprises an upper end and a lower end with a magnet at the lower end.

9. A device according to claim 8, wherein the separation rod comprises a magnet at the lower end thereof and a non-magnetic arm attached to the upper end of the magnet.

10. A device according to claim 7 or 8, wherein the proportion of the length of the magnet to its thickness is at least about 2:1.

11. A device according to claim 10, wherein the separation rod comprises a magnet at the lower end thereof and a ferromagnetic arm attached to the upper end of the magnet.

12. A device according to claim 11, wherein the proportion of the length of the magnet to its diameter is about 10:1 and the proportion of the arm length to the length of the magnet is about 5:1.

13. A device according to claim 12, wherein the arm is thicker than the magnet and the upper end of the magnet is embedded inside the lower end of the arm at a length of about twice the diameter of the magnet.

14. A device according to claim 10, wherein the proportion of the length of the magnet to its thickness is at least about 3:1.

15. A device according to claim 14, wherein the proportion of the length of the magnet to its thickness is at least about 12:1.

16. A device according to claim 7, wherein the protective cover has a cone-shaped tip.

17. A device according to claim 7, wherein the protective cover is tapered and has a sharpended tip with a concave surface.

* * * * *